United States Patent [19]

Svarovsky

[11] 4,179,934

[45] Dec. 25, 1979

[54] METHOD AND APPARATUS FOR MONITORING PARTICLE SIZES

[75] Inventor: Ladislav Svarovsky, Bradford, England

[73] Assignee: University of Bradford, Bradford, England

[21] Appl. No.: 905,944

[22] Filed: May 15, 1978

[30] Foreign Application Priority Data

Jul. 6, 1977 [GB] United Kingdom ............... 29950/77

[51] Int. Cl.² ............................................ G01N 15/02
[52] U.S. Cl. ..................................,............ 73/432 PS
[58] Field of Search ............. 73/432 PS, 61.4; 73/28; 324/71 CP

[56] References Cited

U.S. PATENT DOCUMENTS

| | | | |
|---|---|---|---|
| 3,719,089 | 3/1973 | Kelsall et al. ..................... | 73/432 PS |
| 3,797,319 | 3/1974 | Abe .................................. | 73/432 PS |
| 3,889,180 | 6/1975 | Eichmeier ..................... | 73/432 PS X |
| 4,024,768 | 5/1977 | Leach et al. ..................... | 73/432 PS |

Primary Examiner—Gerald Goldberg
Assistant Examiner—Joseph W. Roskos
Attorney, Agent, or Firm—Stevens, Davis, Miller & Mosher

[57] ABSTRACT

A method for, and apparatus for use in connection with, checking the particle size of a powder entrained in a gas stream, comprising separating a sample of the powder into fractions of relatively different particle sizes and comparing the electrostatic or like noises of the fractions.

11 Claims, 7 Drawing Figures

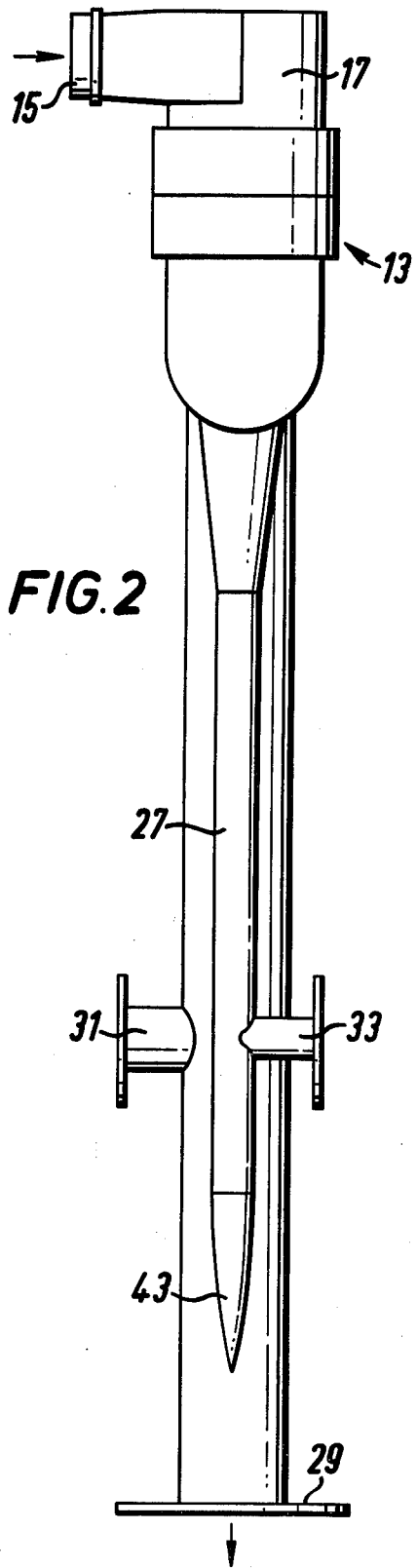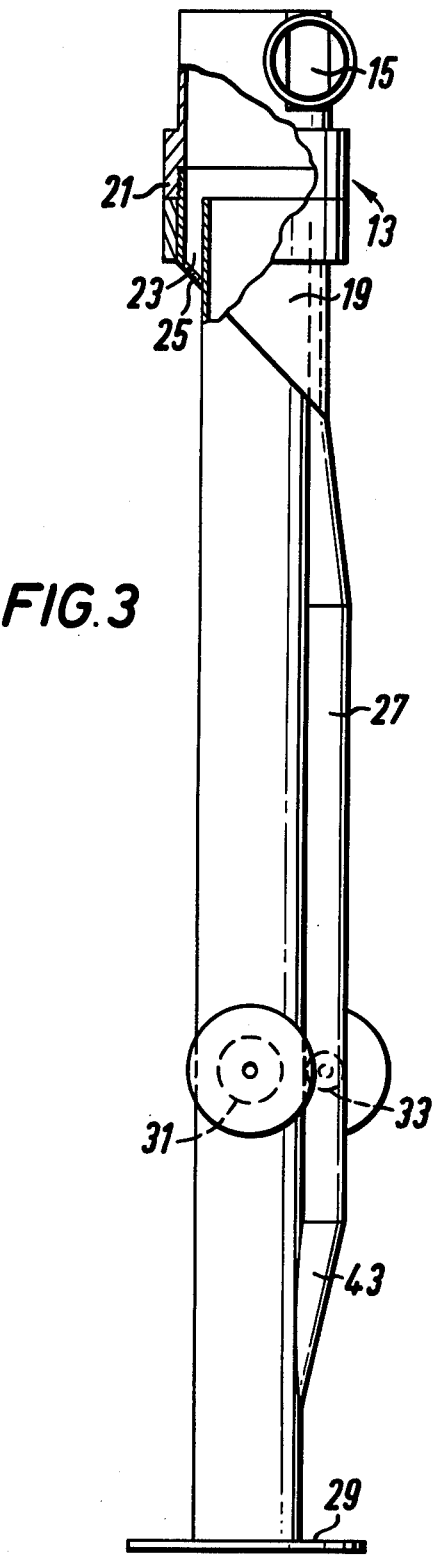

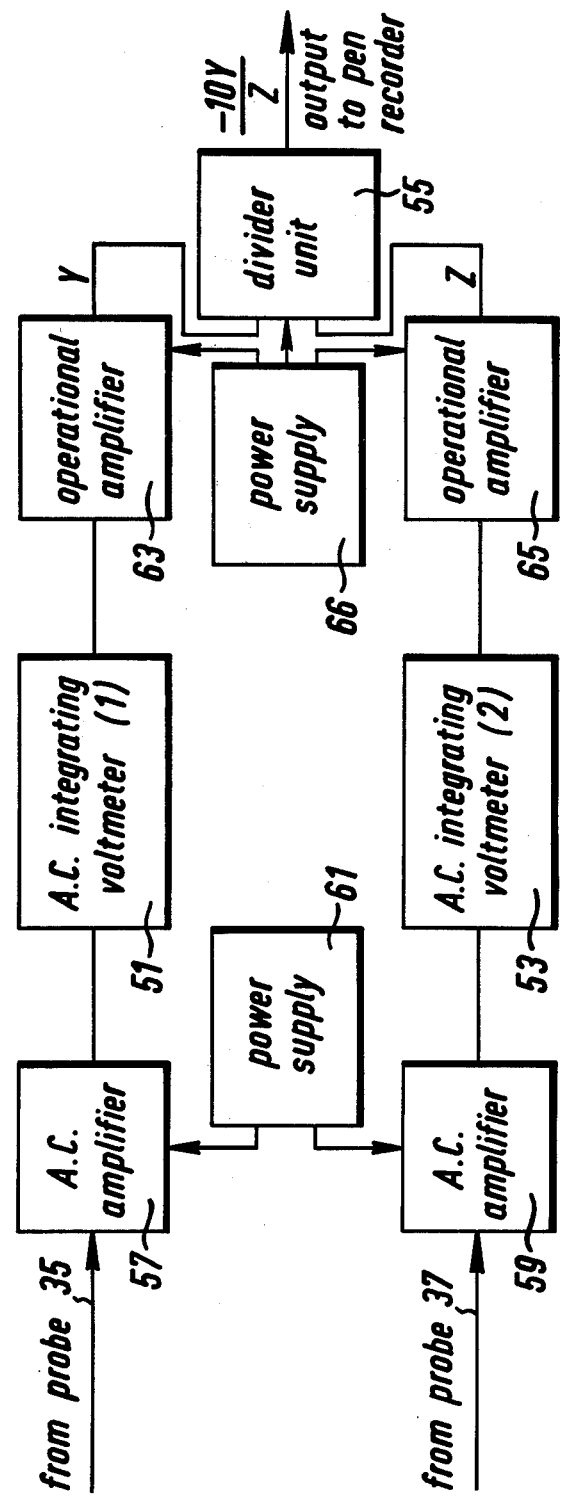

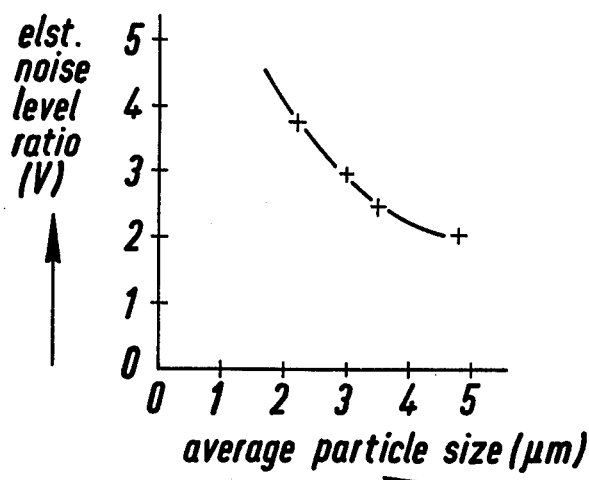
FIG.6 Calibration data from laboratory tests.
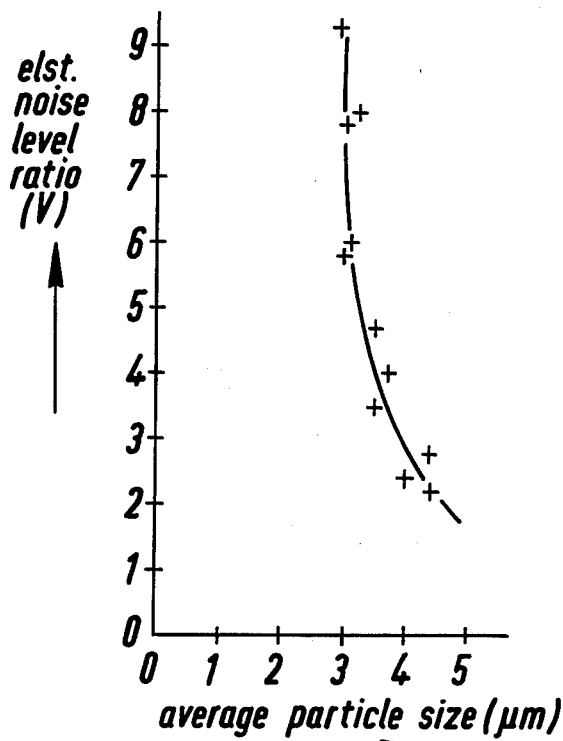
FIG.7 Calibration data from 'in-plant' tests.

METHOD AND APPARATUS FOR MONITORING PARTICLE SIZES

This invention relates to methods and apparatus for monitoring particles entrained in gas streams especially for the purpose of controlling the particle size of particulate matter in process streams.

Automation of process control has created a need for continuous monitoring of the particle size of particulate matter in process streams. Such monitoring can be used to control the process or shut it down altogether if the product is not satisfactory.

Apparatus for monitoring particulate matter in a process stream may be divided into two categories, stream scanning apparatus and filed scanning apparatus. In stream scanning apparatus, which is generally applied to dilute systems, the particles are sent in single file past a detecting device which may be a particle counter based on the Coulter method or a device based on light interruption or scattering method or on the Langer acoustic method.

Field scanning apparatus, which is usually applied to concentrated systems, involves the monitoring of some size-dependent property of the bulk material from which particle size may be deduced from theoretical or calibrated relationships. Examples of field scanning methods are ultrasonic attenuation, echo measurement, laser attenuation and on-line viscometry.

Field scanning methods have advantages over stream scanning methods because in general the former involve the analysis of larger samples thereby reducing sampling errors and also because the particle size is determined from a particular size-dependent property of the particles, and this property can be chosen to be the one most relevant to the ultimate quality of the particular product. However, known filed scanning methods involve the use of expensive equipment which is suitable for only relatively coarse powders and for which the time delay between sample withdrawal and the particle size reading is greater than 1 minute and sometimes as long as 2.5 minutes.

Many industries handle very fine powders, the particle size often being less than 5 $\mu$m and known methods are not suitable for such small particle sizes.

According to the present invention there is provided a method of monitoring particles entrained in a gas stream comprising separating at least a portion of the particles in said gas stream into at least two fractions of relatively different particle sizes and comparing the electrostatic or the like noises of the two or more fractions.

The present invention also provides apparatus for monitoring particles entrained in a gas stream comprising means for separating at least a portion of the particles in said gas stream into at least two fractions of relatively different particle size and means for comparing the electrostatic or the like noises of the two or more fractions.

Electrostatic noise comparing means are preferred, but alternatively means may be provided for comparing other noise, such as capacitance noise or electrical conductivity noise.

Apparatus in accordance with the present invention may provide a voltage ratio readout and this voltage ratio readout can be used together with calibration data to determine the average particle size of the powder in the gas stream.

The method and apparatus of the present invention utilize the principle of differential flow classification (DFC) in which the gas stream or a portion thereof is passed through a separator whose separation efficiency is size dependant. The electrostatic noise of a particular fraction is related to the mass flow rate of the solids in that fraction. The particle size of the solids in that fraction may be determined using the concept of the analytical cut size, according to which the separator is considered as being equivalent to an ideal sieve, that is to say, as if it removes all particles coarser than the cut size into an underflow fraction and all particles finer than the cut size into an overflow fraction. In this way, particle size measurement is reduced to the determination of the mass flow rate or concentration of the solids with the cut size calibrated by a standard laboratory method.

Solid particles, when being conveyed in a turbulent gas stream, acquire electrostatic charge, mainly through triboelectric contact charging. A suitable probe inserted into the gas stream carrying the particles may be used to pick up both DC and AC current components. The former results from the transfer of charge from particle-probe collisions (and also by induction) but the resultant DC current is subject to electrical leakage between the probe and the pipework carrying the gas stream and also due to the surface condition of the probe. However, the AC component, which is the electrostatic noise, is, like the DC component, strongly dependant on the solids concentration in the flow, but it is little affected by leaks or probe surface condition.

Preferably, apparatus in accordance with the present invention includes means for taking off a sample from the gas stream and feeding said sample to said separation means.

Preferably, apparatus in accordance with the invention includes means for feeding the two or more fractions back to the gas stream after the electrostatic noises have been compared. More preferably, means are provided for recombining the two fractions before they are fed back to the gas stream.

Preferably, the apparatus includes means for diluting said sample with air before said sample is fed to said separation means.

Preferably, the separation means comprises a cyclone device.

Preferably, the electrostatic noise comparing means comprise electrodes located in the path of respective ones of said fractions and means connected to said electrodes for amplifying the AC components of the signals of the electrodes.

Apparatus in accordance with the present invention may include means for comparing "noise" other than electrostatic noise. For instance, the apparatus may include means for measuring capacitance noise or electrical conductivity noise.

Separators other than cyclone type separators may be used. For instance, a louvre separator may be used for relatively large particle sizes.

Apparatus in accordance with the present invention will now be described, by way of example only, with reference to the accompanying drawings, in which:

FIG. 2 is a front elevation of a separator suitable for use with the apparatus in accordance with the present invention;

FIG. 3 is a side elevation of the separator of FIG. 2;

FIG. 5 is a schematic diagram of the electronic circuit for apparatus in accordance with the present invention;

FIG. 6 shows a calibration curve obtained with a silica powder; and

FIG. 7 is a further calibration curve obtained with a silica powder.

Figure 1:
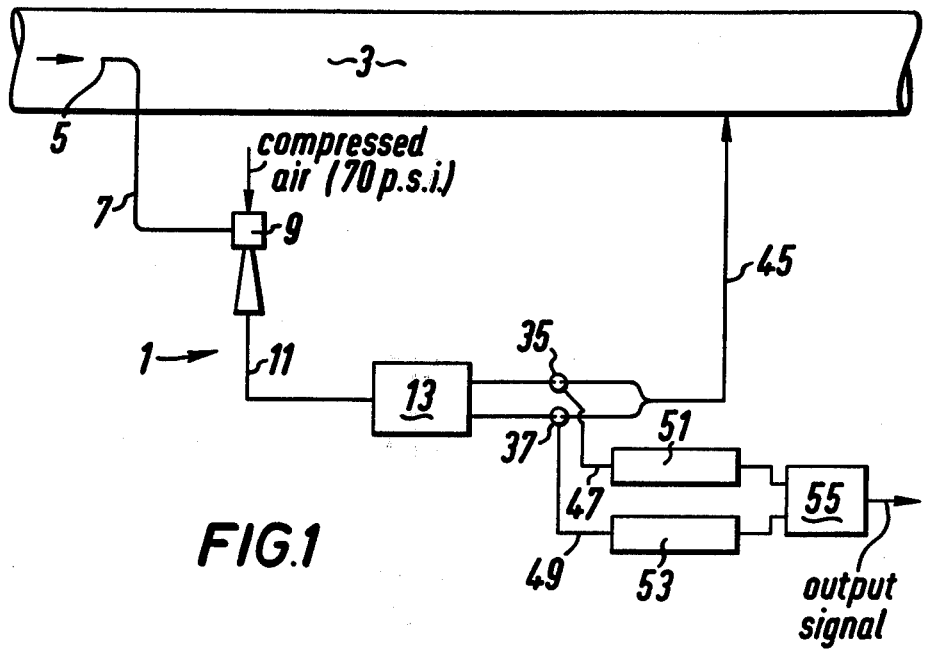
FIG. 1 is a schematic diagram of apparatus in accordance with the present invention.

Referring to FIG. 1, apparatus in accordance with the present invention shown generally by numeral 1 is illustrated fitted to a pipe 3 carrying the production stream from a particle manufacturing process. The apparatus includes a sampling probe 5 which separates a portion of the gas stream and the separated portion is fed along pipe 7 to a so-called ejector 9 at which compressed air may be injected into the separated portion so as to dilute the solids and also provide the driving force through the remainder of the apparatus. The diluted gas stream portion is then fed along pipe 11 to the separator 13. This splits the portion into two fractions, namely, a relatively large air stream containing a low concentration of solids (overflow with fine product) and a relatively small air stream with a high concentration of solids (underflow with coarse product).

A suitable separator 13 is shown in FIGS. 2 and 3. In this case, the separator is a small "uni-flow" cyclonic device having a cut size in the range from 2 to 5 μm. Separator 13 includes an inlet 15 which extends transversely from a substantially cylindrical body portion 17. The gas stream carrying particles enters the cyclone through inlet 15 which, as shown best in FIG. 3, is offset from the longitudinal axis of the cyclone body. Accordingly, the gas stream within the body is caused to rotate so that the heavier particles tend to accumulate near the wall of the cyclone body, whereas the lighter particles tend to remain nearer the longitudinal axis of the device. As the swirling gas stream progresses in a direction away from the inlet it is divided into two by means of the coaxial arrangement of pipes 19 connected to the cyclone body 17 by means of ring 21. The outer pipe 23 is of comparatively short length with a tapered end 25 remote from inlet 15. The furthest point of tapered end 25 of inner pipe 19 connects with a pipe 27 of relatively narrow diameter which is mounted on inner pipe 19. In this way, the particle laden gas stream entering inlet 15 is separated into two streams, one of which enters pipe 27 and carries most of the solid particles suspended in about 10 percent of the total air flow whilst the other contains the fine, unseparated solids and enters pipe 19.

Figure 4:
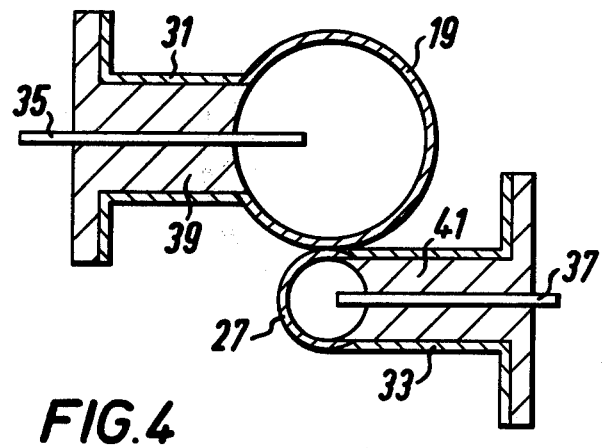
FIG. 4 is a cross-section through the separator of FIG. 2 at the position of the probes and showing the probes in position.

At a position about two-thirds of the distance from separator 13 to the end 29 of pipe 19, remote from separator 13, each pipe 19 and 27 is provided with a respective probe inlet 31 and 33. As shown in FIG. 4, each inlet 31, 33 is provided with a respective probe 35, 37 in the form of an electrode. Probes 35, 37 extend to a position close to the longitudinal axis of their respective pipes and each probe 35, 37 is mounted in its respective inlet 31, 33 by means of an insulator 39, 41.

At a position between inlets 31 and 33 and end 29 of pipe 19, pipe 27 terminates at end 43, end 43 being in communication with pipe 19 so that its gas stream with entrained solids passes back into pipe 19.

The recombined gas stream fractions are then returned to pipe 3 along pipe 45 (see FIG. 1).

It should be understood that since the pressure drop across the cyclone is a unique function of the gas flow rate (at low solids concentrations), the calibration flow rate is maintained in use by maintenance of a constant pressure drop across the separator if the pressure and temperature in the production line remain constant.

Each of the probes 35, 37 may be a 4BA screw which may serve as a simplified form of threaded rod electrode. These electrodes are connected via lines 47 and 49 to electronic components of which only respective AC integrating voltmeters 51 and 53 together with divider unit 55 are shown in FIG. 1. The electronic circuit is shown in more detail in FIG. 5 and it will be seen that the basic elements include respective AC amplifiers 57 and 59 connected to power supply 61. Each AC amplifier 57, 59 is a variable gain amplifier which amplifies the AC noise voltage which appears on the probe into a measurable noise voltage. The amplifiers are placed very close to their respective probes and the wires connecting the probes to their respective amplifiers are screened by a metal casing earthed to the rig wall to minimize the pickup of the mains hum and other unwanted interfering signals.

The amplified signals are fed as inputs to respective AC integrating voltmeters 51 and 53. These have a smoothing circuit with a variable time constant so that the AC noise voltage is converted into a reasonably noiseless voltage proportional to the noise level. The output signals from the AC integrating voltmeters 51 and 53 are fed to respective operational amplifiers 63 and 65 and the outputs therefrom are fed to the divider unit 55 (the amplifiers 63 and 65 and divider unit 55 being connected to a power supply 66), the output of which is the required voltage ratio V given by the following relationship:

$$V = -10 Y/Z$$

where

V = the voltage ratio (in volts)
Y = voltage picked up by probe 35
Z = voltage picked up by probe 37.

The output from divider unit 55 is either recorded on a pen recorder or used directly as a control signal for regulating or shutting off the process for producing the particles in the original gas stream.

The above-described separator 13 is designed to operate at a gas flow rate of 29 m$^3$/hour which corresponds approximately to 100 mm WG (column of water) with a solids concentration of less than 5 g/m$^3$. The necessary dilution is achieved by the introduction of ambient air in the ejector 9 and by adjustment of the size of the aspiration nozzle (not shown) at the tip of the sampling probe 5.

The above-described apparatus has to be calibrated for every type of solid particle with which it is going to be used. FIGS. 6 and 7 are examples of calibration curves obtained with a silica powder in a laboratory test rig and in a plant respectively. The average particle size (the median) was measured by Coulter Counter. As can be seen, the sensitivity of the apparatus was in this particular case better on the plant than in the laboratory, most probably due to higher levels of particle static charge.

In use, the signal from the divider unit 55 is converted into average particle size using the appropriate calibration curve. This can be done automatically using a processor or alternatively, if the same product is to be used all the time, the signal can be used directly for control purposes without conversion and the calibration of the analyser can be included in the calibration of the whole control system.

By means of the above-described apparatus, the particle stream may be monitored continuously and any variation in quality, which will be reflected by a change in particle size, may be virtually instantaneously determined and appropriate adjustments or shut down of the process can be carried out, either automatically or otherwise.

I claim:

1. Apparatus for monitoring particles entrained in a gas stream, said particles having an electrical noise associated therewith, the characteristic of said electrical noise being related to the size of said particle, comprising means for separating at least a portion of the particles in said gas stream into at least two fractions of relatively different average particles sizes and means for comparing the electrical noise associated with the two or more fractions.

2. Apparatus according to claim 1 wherein the means for comparing the electrical noise of the two or more fractions comprise means for comparing the electrostatic noises of these fractions.

3. Apparatus according to claim 1 and including means for taking a sample from said stream and feeding said sample to said separation means.

4. Apparatus according to claim 3 wherein means are provided for feeding the two or more fractions back to the said stream after the electrical noise have been compared.

5. Apparatus according to claim 4 wherein means are provided for recombining the two fractions before they are fed back to the said stream.

6. Apparatus according to claim 3 and including means for diluting said sample with air before said sample is fed to said separation means.

7. Apparatus according to claim 1 wherein said separation means comprises a cylcone device.

8. Apparatus according to claim 1 wherein the electrical noise comparing means comprise electrodes located in the path of respective ones of said fractions and means connected to said electrodes for amplifying the AC components of the signals of the electrodes.

9. An apparatus according to claim 1, wherein the means for comparing the electrical noise associated with the two or more fractions provides a comparison of the AC components of the electrical noise of each fraction.

10. A method of monitoring particles entrained in a gas stream comprising separating at least a portion of the particles in said gas stream into at least two fractions of relatively different particle sizes and comparing the electrical noise associated with the two or more fractions.

11. A method according to claim 10 wherein the electrical noise comparing means are means for comparing the electrostatic noises of the said fractions, and the method includes the steps of taking a sample from the gas stream, diluting said sample with air, feeding the diluted sample to said separation means and feeding the two or more fractions back to said gas stream after the noises have been compared.

* * * * *